United States Patent [19]

Nappa et al.

[11] Patent Number: 5,672,788
[45] Date of Patent: Sep. 30, 1997

[54] TWO-STEP PROCESS FOR MANUFACTURING 1,1-DIFLUOROETHANE

[75] Inventors: Mario Joseph Nappa, Newark; Klaus Guenter Wuttke, Wilmington, both of Del.

[73] Assignee: E. I. Du Pont de Nemours and Company, Wilmington, Del.

[21] Appl. No.: 476,770

[22] Filed: Jun. 7, 1995

[51] Int. Cl.⁶ .......................... C07C 17/087; C07C 17/20
[52] U.S. Cl. ..................................... 570/168; 570/248
[58] Field of Search ........................... 570/168, 248

[56] References Cited

U.S. PATENT DOCUMENTS

| | | | |
|---|---|---|---|
| 2,452,975 | 11/1948 | Whalley | 570/168 |
| 2,495,407 | 1/1950 | Chapman et al. | 260/653 |
| 3,190,930 | 6/1965 | Brock et al. | 260/653.6 |
| 3,707,574 | 12/1972 | Stephan et al. | 570/248 |
| 3,862,995 | 1/1975 | Martens et al. | 200/653.6 |
| 3,904,701 | 9/1975 | Schultz et al. | 570/166 |
| 4,147,733 | 4/1979 | Fiske et al. | 260/653.4 |
| 4,766,258 | 8/1988 | Komatsu et al. | 570/168 |
| 5,008,474 | 4/1991 | Wairseveas et al. | 570/168 |
| 5,155,082 | 10/1992 | Tung et al. | 502/228 |
| 5,208,395 | 5/1993 | Elsheikh | 570/166 |
| 5,396,001 | 3/1995 | Peanstreau | 870/179 |

FOREIGN PATENT DOCUMENTS

| | | | |
|---|---|---|---|
| A648783 | 12/1964 | Belgium . | |
| 832502 | 1/1970 | Canada . | |
| 1074434-A | 7/1993 | Canada . | |
| 1069019a | 2/1993 | China . | |
| 0 187 643 | 4/1989 | European Pat. Off. . | |
| 637 579 A1 | 4/1993 | European Pat. Off. . | |
| 0 547 930 A1 | 6/1993 | European Pat. Off. . | |
| 0 606 482 a1 | 7/1994 | European Pat. Off. . | |
| 0 637 579 A1 | 2/1995 | European Pat. Off. . | |
| 0 676 386 A1 | 10/1995 | European Pat. Off. . | |
| 0 693 469 A1 | 1/1996 | European Pat. Off. . | |
| 48-16487 | 5/1973 | Japan . | |
| 106905 | 8/1975 | Japan | 570/168 |
| 53-116304 | 10/1978 | Japan . | |
| WO94/22796 | 10/1994 | Japan . | |
| 341788 | 6/1972 | U.S.S.R. . | |
| 423789 | 4/1974 | U.S.S.R. . | |
| 466202 | 4/1975 | U.S.S.R. . | |
| 454128 | 9/1936 | United Kingdom | 570/248 |
| 1178284 | 8/1967 | United Kingdom | 570/168 |
| WO94/23813 | 10/1994 | WIPO . | |
| WO94/22797 | 10/1994 | WIPO . | |

OTHER PUBLICATIONS

Rinker & Corcoran, Catalytic Addition of Hydrogen Chloride to Vinyl Chloride, *I & ED Fundamentals*, 6, pp. 333–338, Aug. 1967.

Stanley M. Walas, Phase Equilibriua In Chem. Eng. *Butterworth Publishers*, 165–244, 1985.

*Primary Examiner*—C. Warren Ivy
*Assistant Examiner*—Lyman H. Smith

[57] ABSTRACT

A process is disclosed for producing 1,1-difluoroethane ($CH_3CHF_2$ or HFC-152a) in a two-step reaction in a manner that reduces formation of high boiling materials. The first step comprises adding at least one of HCl or HF to chloroethene ($CH_2=CHCl$) in order to obtain at least one of 1,1-dichloroethane ($CH_3CHF_2$) or 1-chloro-1-fluoroethane ($CH_3CHClF$). The second step comprises converting 1,1-dichloroethane or 1-chloro-1-fluoroethane to 1,1-difluoroethane.

8 Claims, 1 Drawing Sheet

1

TWO-STEP PROCESS FOR MANUFACTURING 1,1-DIFLUOROETHANE

FIELD OF THE INVENTION

The instant invention relates to a process for producing 1,1-difluoroethane ($CH_3CHF_2$ or HFC-152a) in a two-step reaction in a manner that reduces formation of high boiling materials. The first step comprises adding at least one of HCl or HF to chloroethene ($CH_2=CHCl$) in order to obtain at least one of 1,1-dichloroethane ($CH_3CHCl_2$) or 1-chloro-1-fluoroethane ($CH_3CHClF$). The second step comprises converting 1,1-dichloroethane or 1-chloro-1-fluoroethane to 1,1-difluoroethane.

BACKGROUND 1,1-difluoroethane ($CHF_2CH_3$ or HFC-152a) can be manufactured either by a liquid phase or gas phase process.

Elsheikh (U.S. Pat. No. 5,208,395) discloses a gas phase process for producing HFC-152a from 1,1-dichloroethane (HCC-150a) and hydrogen fluoride in the presence of solid tin tetrafluoride on activated carbon.

Ozawa et al. (Japanese Patent Application Kokai No. 50-106905) discloses a liquid phase process to make HFC-152a from HCC-150a and HF using an antimony pentafluoride catalyst.

Golubev et al. (Soviet Inventor Certificate No. 341788) discloses a liquid phase process for reacting chloroethene with hydrogen fluoride to form HFC-152a.

Guofei et al. (People's Republic of China Patent Application Publication No. 1069019a) disclose a liquid phase process at a lower temperature (0° to 70° C.), in order to increase the selectivity for HFC-152a.

Several methods are known for converting chloroethene to 1-fluoro-1-chloroethane (HCFC-151a). Chapman et al. (U.S. Pat. No. 2,495,407) discloses a process using a tin tetrachloride catalyst and operated between 10 and 80 deg. C.

HCl can be added to chloroethene to make HCC-150a ($CHCl_2CH_3$) as disclosed by Rinker and Corcoran (Rinker, R. G. and Corcoran, W. H. "I&EC Fundamentals 6", 333 8, 1967F).

The disclosure of the previously identified references is hereby incorporated by reference.

SUMMARY

In conventional processes for making HFC-152a there is a trade-off between high production rates of HFC-152a and minimal formation of high boiling materials. Minimizing the formation of high boiling materials is important for industrial production since the materials interfere with the catalyst, fill up reactor space, decrease the yield of the desired product, and must be treated for disposal.

High production rates of HFC-152a can be achieved in the inventive process by using a catalyzed liquid phase process. The instant invention solves the problems associated with conventional method for making HFC-152a at high yields while minimizing formation of undesired high boiling materials.

The instant invention relates to a process for making HFC-152a, which has a reduced rate of tar formation in the fluorination process, that is achieved by using a two-step process. A starting material comprising chloroethene is converted to one or more saturated intermediates, such as 1,1-dichloroethane (HCC-150a) or 1-chloro-1-fluoroethane (HCFC-151a), under conditions that minimize tar formation. A final product comprising 1,1-difluoroethane (HFC152a) is then produced by contacting at least one intermediate and hydrogen fluoride while in the presence of catalyst comprising tin tetrahalide. Conversion of chloroethene can be at least about 95%, and the yield of high boilers and tars can be reduced to less than about 0.5% by weight based on chloroethene fed to the reactor.

CROSS REFERENCE TO RELATED PATENT APPLICATIONS

The subject matter of the instant invention is related to commonly assigned and copending U.S. patent application Ser. No. 08/468,099 (Attorney Docket Number CH-2511), filed on Jun. 5, 1995 in the names of Maria Beug-Deeb et al. and entitled "Azeotropic and Azeotrope-like Compositions of HF and Dihaloethanes".

The instant invention is also related to commonly assigned and copending U.S. patent application Ser. No. 08/474,884 (Attorney Docket Number CH-2512), filed on even date herewith in the name of Klaus G. Wuttke and entitled "Continuous Manufacture of 1,1-Difluoroethane".

The subject matter of the instant invention is also related to U.S. patent application Ser. No. 08/480,066 (Attorney's Docket No. CH-2530), filed on even date herewith in the names of Wendel R. Cassel et al. and entitled "Manufacture of 1,1-Difluoroethane by Reactive Distillation".

The disclosure of the aforementioned patent applications is hereby incorporated by reference.

DETAILED DESCRIPTION

Figure 1:
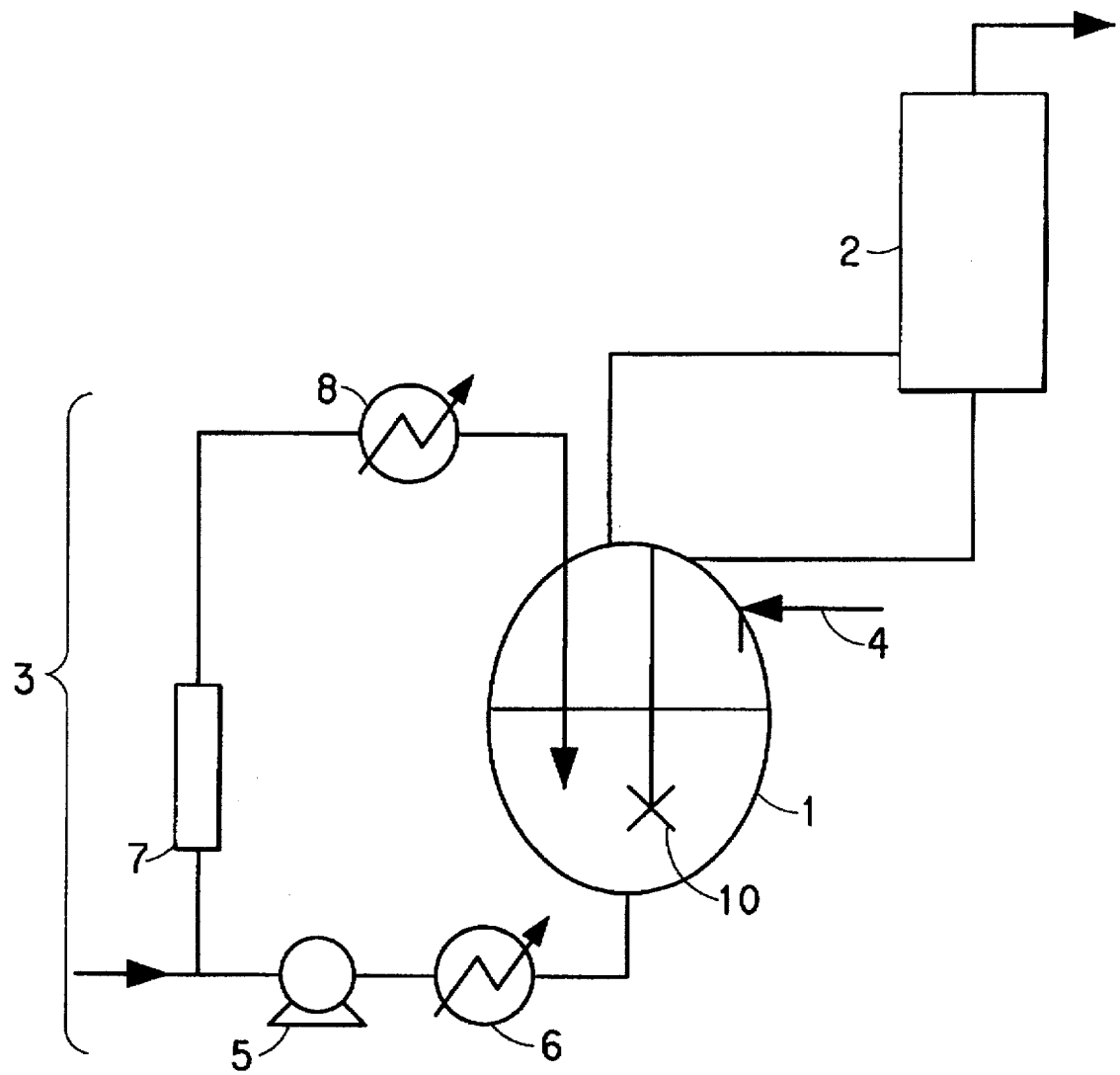
FIG. 1—FIG. 1 is a schematic of a system of apparatus which includes a pump-around loop that can be employed to practice one aspect of the inventive process.

Hydrofluorocarbons (HFCs) such as 1,1-difluoroethane can be an environmentally acceptable replacements for certain chlorofluorocarbons (CFCs). 1,1-difluoroethane ($CHF_2CH_3$ or HFC-152a) may be employed alone or in blends as a refrigerant, cleaning agent, blowing agent for thermoplastic or thermoset foams, an aerosol propellant, a heat transfer media, gaseous dielectrics, power cycle working fluids, polymerization media, particulate removal fluids, carrier fluids, buffing abrasive agents, displacement drying agents, an intermediate for other fluorinated compounds such as vinyl fluoride, among other applications.

1-chloro-1-fluoroethane ($CHClFCH_3$, HCFC-151a) and 1,1-dichloroethane ($CHCl_2CH_3$, HCC-150a) are potential intermediates to other fluorocarbon compounds such as at least one of vinyl fluoride, 1,1,1-trichloroethane, among other desirable compounds.

High production rates of HFC-152a can be achieved by using the inventive catalyzed liquid phase process. The inventive process comprises a process for making 1,1-difluoroethane in a two-step reaction which minimizes, if not eliminates, the formation of tars. In the first step of the inventive process, chloroethene ($CH_2=CHCl$ or vinyl chloride) is hydrohalogenated under conditions that minimize tar formation to form one or more intermediates comprising or consisting essentially of 1,1-dichloroethane and 1-chloro-1-fluoroethane. In the second step of the process, at least a portion of the chlorine atoms on 1,1-dichloroethane and/or 1-chloro-1-fluoroethane structures are substituted with fluorines atoms to produce 1,1- difluoroethane. If desired, 1,1-difluoroethane production rates can be increased by increasing the reaction temperature, e.g., up to about 95 C., while maintaining tar formation to a very low level.

The rate of tar formation is defined as the weight of high boiling materials formed in the reactor divided by the weight of starting material feed. By "high boiling materials" or "tars", it is meant molecules formed by coupling at least two chloroethene units. Typically, tars are characterized by an average molecular weight of about 1,000 to 30,000. The amount of high boiling materials includes both the tars that are soluble and insoluble in the organic phase. Total tar formation is expressed in amount of tar per amount of chloroethene fed (usually pounds or tar/100 pounds chloroethene).

The products of the first step or HFC-152a intermediates can be obtained from any suitable source. For example, HCFC-151a can be produced by using a liquid phase reaction with a tin tetrachloride catalyst such as described by Chapman et al. (U.S. Pat. No. 2,495,407); the disclosure of which is hereby incorporated by reference. To operate a process for making HCFC-151a, a reactor is equipped with a reflux column. Predetermined amounts of HF and $SnCl_4$, e.g., about 5 to at least about 35 weight % $SnCl_4$ in HF) are added to the agitated reactor. If desired, the conversion of chloroethene to HCFC-151a can be increased by increasing the concentration of catalyst in the liquid phase. The system is heated a temperature of about 0 to about 50 deg. C., and brought to reflux at the desired operating pressures of about 0 to about 50 psig. Liquid anhydrous HF and the chloroethene are fed into the reactor. Gas exiting from the reactor enters a reflux column that is operated at a reflux ratio between about 2 and about 10. The gas stream leaving the reflux condenser typically consists essentially of HCFC-151a, e.g., the stream contains about 60 to about 80 wt. % HCFC-151a depending upon the temperature of the reflux condenser.

HCFC-151a can also be obtained from chloroethene in a liquid phase process by using a fluoride catalyst. Examples of this catalyst comprise at least one of sodium fluoride, cesium fluoride, ammonium fluoride, among others. Alternatively, the catalyst can be formed in situ by reacting an appropriate Lewis base with HF, e.g., reacting tertiary amines with HF. An agitated reactor is loaded with an ammonium fluoride catalyst and HF, e.g., about 1 to about 10 weight % ammonium fluoride in I-IF. Anhydrous HF and chloroethene are added either continuously or in batch mode to a reactor having conventional design, e.g., HF containing less than about 20 ppm water is added to the reactor. Gas exiting from the reactor enters a commercially available reflux column. The gas stream leaving the reflux condenser consists essentially of HCFC-151a and HF. Tar formation is less than about 0.1% by weight of the chloroethene feed. Without wishing to be bound by any theory or explanation, it is believed that the anionic nature of the bifluoride catalyst avoids polymerization and, therefore, minimizes the formation of tars.

HCC-150a can also be obtained by any suitable process. For example, HCC-150a can be made in high yield and with little tar formation by adding HCl to chloroethene as described by Rinker, R. G. and Corcoran, W. H. "I&EC Fundamentals 6", 333 8, 1967F; the disclosure of which is hereby incorporated by reference.

Regardless of the method for making the HCFC-151a and HCC- 150a intermediates, the intermediate(s) can be characterized by a purity of at least about 80 to 98% by weight.

The second step, also referred to herein as the halogen replacement step, comprises substituting the chlorine atoms on the HCFC-151a and/or HCC-150a intermediates with fluorine atoms to produce HFC-152a. For this step of the process, a reactor is equipped with a reflux column; both of which are commercially available. Predetermined amounts of HF and $SnCl_4$, e.g., about 5 to about 35 weight % $SnCl_4$ in HF are added to an agitated reactor. While any suitable means can be employed for agitating the reactor, typically the agitation means comprises a mechanically driven agitator. The contents within the reactor are heated to a temperature of about 50 to 150 deg. C., and brought to reflux at the desired operating pressures, e.g., typically about 50 to 400 psig. After the desired reflux flow is reached, both liquid anhydrous HF and the organic feed, i.e., comprising HCFC-151a and/or HCC-150a, are introduced into the reactor. Gas exiting from the reactor enters the reflux column which is operated at a reflux ratio between about 2 and 10. The gas stream leaving the reflux column typically consists essentially of equimolar amounts of HFC-152a and HCl, e.g., less than about 5% HF and trace amounts of vinyl chloride, HCFC-151a and HCC-150a.

The inventive two-step process can be operated either in a continuous mode or as a batch operation in many configurations. For a continuous process, a starting material comprising vapor or liquid (normally vapor) chloroethene reacts with vapor or liquid HF and HCl in a first reactor to form HCFC-151a and/or HCC-150a. While any suitable source of chloroethene can be employed, for best results the chloroethene comprises or consists essentially of a material that has a purity which is sufficient to avoid introducing contaminants into the process, e.g., such contaminants may be carried through the process into the desired product. The first and second process steps are typically practiced with an excess amount of HF. That is, in excess of the stoichiometric amounts required to obtain the desired product. The HCFC-151a and HCC-150a intermediates can then be refluxed from the first reactor into a second reactor comprising a liquid phase mixture of HF and $SnCl_4$ catalyst, e.g., about 1 to about 30wt % $SnCl_4$ in HF. The reflux ratio of the first reactor reflux column is about 1 to about 20. HF is fed continuously into the reactors while the liquid phase is being agitated. Gas from the second reactor enters a reflux column and the gas stream leaving the reflux condenser consists essentially of equimolar amounts of HFC-152a and HCl, or HFC-152a and 2 moles of HCl depending upon whether HF or HCl was reacted with chloroethene.

Referring now to the FIGURE, FIG. 1 illustrates one aspect of the inventive two-step process for making HFC-152a. A reactor 1 is equipped with a reflux column 2 and a pump-around loop that is referred broadly to as 3. In this aspect of the invention, the addition step can be performed in the pump-around loop 3, while the halogen replacement step can be achieved in the reactor 1. A liquid phase comprising HF and $SnCl_4$ are added via conduit 4 to reactor 1 having an agitator 10. The contents of reactor 1 are heated to a temperature of about 50 to about 150 deg. C., and brought to reflux at the desired operating pressures, e.g., about 50 to about 400 psig. HF can be fed continuously via conduit 4 to reactor 1. A portion of the liquid phase within reactor 1 is transported by pump 5 through a first heat exchanger 6, a static mixer 7, a second heat exchanger 8 and back into the reactor 1, e.g., below the surface of the liquid phase within reactor 1. Pump 5 transports the fluid withdrawn from reactor 1 at a rate of about 0.01 to about 0.5 reactor volume units. The first heat exchanger 6 maintains the temperature within loop 3 at about 0 to about 50 deg. C.

Chloroethene is introduced via conduit 9 into the fluid withdrawn from reactor 1 at a location prior to contact with the static mixer 7. The chloroethene-containing mixture is heated to the reactor temperature when it passes through the second heat exchanger 8. The residence time for the mixture in the loop 3 before reaching the second heat exchanger 8 is preferably sufficient to convert the chloroethene in the mixture, as well as any intermediates, into 1,1-difluoroethane.

The production equipment illustrated in FIG. 1 is commercially available and of conventional design. The production equipment and its associated feed lines, effluent lines and associated units should be constructed of materials resistant to HF and HCl. Typical materials of construction, well-known to the fluorination art, include stainless steels and the well-known high nickel alloys, such as Monel® nickel-copper alloys, Hastelloy® nickel-based alloys and, Inconel® nickel-chromium alloys.

Specific examples illustrating the certain aspects of the inventive process are shown below. It is to be understood that these examples are merely illustrative and in no way are to be interpreted as limiting the scope of the invention as defined in the appended claims.

EXAMPLE 1

1st STEP (Addition of HF to chloroethene using SnCl$_4$)

In a drybox, approximately 5 grams of SnCl$_4$ was charged to a 600 cc Parr autoclave. The autoclave was then sealed and attached to a gas handling system capable of continuously feeding HF and chloroethene (CH$_2$=CHCl, vinyl chloride). About 95 grams of anhydrous HF were pumped into the autoclave. The resulting solution in the autoclave was left overnight.

Next, chloroethene was fed into the autoclave as a vapor through a dip leg at a feed rate of approximately 30 g/hr over a period of about 55 hours. The solution in the autoclave was maintained at about 20 deg C. and 20 psig, wherein a constant solution mass was maintained by adding HF. The vapor effluent from the autoclave passed through a reflux condenser which was placed above the reactor, and the reflux condenser was held at a temperature of about 14 deg C. using a glycol/water recirculating bath.

After setting the HF feed rate such that a substantially constant reactor mass was maintained and after several consecutive gas chromatographic (GC) analysis within experimental error, the GC analysis of the reflux condenser effluent showed yields of approximately 9% HFC-152a (CHF$_2$CH$_3$), 38% HCFC-151a (CHFClCH$_3$), and 2% HCC-150a (CHCl$_2$CH$_3$). Between 50 and 51% of the chloroethene passed through the reactor and condenser unreacted.

After the run, the volatile components (predominantly HF, HCl, HCC-150a, HCFC-151a, and HFC-152a) remaining in the solution within the reactor were removed by bubbling nitrogen through the solution overnight. After washing the removed volatile components with water and dichloromethane (CH$_2$Cl$_2$) solutions, solid tars were isolated and dried. The dried tars from the water solution had a mass of approximately 0.69 g. The solution CH$_2$Cl$_2$ was evaporated and about 2.4 g of tars were collected. The total amount of tar collected from the water and dichloromethane solutions was about 3.09 g that corresponds to a tar formation rate of about 0.19% g tars per g of chloroethene feed.

EXAMPLE 2

Alternative 1st Step (Addition of HF to chloroethene using bifluoride)

Liquid anhydrous HF (about 110 g), chloroethene (about 60 g), and ammonium bifluoride (about 10 g) were added to a Parr bomb and allowed to react for about 16 hours at a temperature of about 30 deg C. under the vapor pressure of the contents. The volatile contents (108 gm) exiting from the Parr bomb were vented through two caustic scrubbers, a drier, and then a cold trap (−78 deg C.). The contents of the cold trap were analyzed by gas chromatography (GC) and determined to correspond on a wt. % basis approximately to:

| HFC-152a | 1.0% |
|---|---|
| chloroethene | 1.0% |
| HCFC-151a | 97.1% |
| HCC-150a | 1.3% |

A slightly yellow liquid contents from the reactor were placed into a shaker tube (approximately 111 gm), and drowned on ice. While the contents were yellow in color, there was no evidence of tar formation other than a slight scum on the surface of the water layer. The organic layer in the tube was collected (approximately 69 gm), analyzed by gas chromatography, and found to correspond on a wt. % basis to:

| chloroethene | 2.6% |
|---|---|
| HCFC-151a | 96.7% |

This also corresponds to an HCFC-151a yield of about 81%. No tar formation was observed during the analysis.

EXAMPLE 3

2nd STEP (conversion of HCFC-151a to HFC-152a)

SnCl$_4$ (approximately 2.6 gm, 0.01 mol) was added to a Hastelloy® C 450 cc Parr Series 4560 Mini Reactor that was located within a dry box. The reactor head, which was equipped with a ¼" tube reflux condenser, was attached to the reactor. The reactor was removed from the drybox. The reactor head was then connected to a stainless steel vacuum line. The bottom of the reactor was immersed in liquid nitrogen, and HF (150 gm, 7.5 mol) was transferred from a 4 lb cylinder into the reactor. The liquid nitrogen was removed, the temperature of the reactor was raised by using external heating (hot air gun) until the internal temperature was about 25 deg C., and cooling water (about −3.7° C.) was passed through the condenser. A fabric heating jacket was put around the reactor and the internal temperature of the reactor was raised to about 50 deg C., at which time a flow of HCFC-151a was begun (about 35 standard cubic cm/minute or sccm, 6.42 ml/hr). In addition to continuously feeding HCFC-151a to the reactor, methane gas (10 sccm) was fed and used as an internal standard.

After about 4.3 hours, a gaseous effluent exiting the reactor was analyzed by gas chromatography and determined to correspond on a mole % basis to:

| Vinyl fluoride | 7.1% |
|---|---|
| HFC-152a | 85.1% |
| chloroethene | 7.5% |
| HCFC-151a | 4% |

When the contents of the reactor were discharged, there was a small amount of water soluble black glaze remaining in the reactor; but no water insoluble tars were detected.

EXAMPLE 4

2nd STEP (Conversion of HCC-150a to HFC-152a)

SnCl$_4$ (approximately 2.6 gm, 0.01 mol) was added to a Hastelloy® C 450 cc Parr Series 4560 Mini Reactor that was located in a dry box. A reactor head, which was equipped with a small ¼" tube reflux condenser, was attached to the reactor. The reactor was removed from the drybox. The reactor head was connected to a stainless steel vacuum line. The bottom of the reactor was immersed in liquid nitrogen, and HZF (approximately 150 gm, 7.5 mol) was transferred from a 4 lb cylinder into the reactor. The liquid nitrogen was removed, the temperature of the reactor was raised by using external heating (hot air gun) until the internal temperature of the reactor was about 25 deg C., and cooling water (about −3.7 deg C.) was passed through the condenser. A fabric heating jacket was placed around the reactor, and the internal temperature of the reactor was increased to about 50 deg C., at which time a flow of HCC-150a was begun (about 37.2 sccm, 7.68 ml/hr). In addition to continuously feeding the HCC-150a into the reactor, methane gas (about 10 sccm) was fed and used as an internal standard.

After about 8.75 hours, a gaseous effluent exiting the reactor was analyzed by gas chromatography and determined to correspond on a mole % basis to:

|             |       |
|-------------|-------|
| Vinyl fluoride | 5.4%  |
| HFC-152a    | 81.0% |
| chloroethene | 11.9% |
| HCFC-151a   | 1.2%  |

When the contents of the reactor were discharged, there was a small amount of water soluble black liquid (less than about 100 mg) remaining in the reactor; but no water insoluble tars were detected.

COMPARATIVE EXAMPLE 1

Chloroethene to HFC-152a

SnCl$_4$ (approximately 2.6 gm, 0.01 mol) was added to a Hastelloy® C 450 cc Parr Series 4560 Mini Reactor that was located in a dry box. The reactor head, which was equipped with a small ¼" tube reflux condenser, was attached to the reactor. The reactor was removed from the drybox. The reactor head was connected to a stainless steel vacuum line. The bottom of the reactor was immersed in liquid nitrogen, and HF (about 150 gm, 7.5 mol) was transferred from a 4 lb cylinder into the reactor. The liquid nitrogen was removed, the temperature of the reactor was raised by using external heating (hot air gun) until the internal temperature was about 25 deg. C, and cooling water (about −3.7 deg. C.) was passed through the condenser. A fabric heating jacket was placed around the reactor and the internal temperature of the reactor was raised to about 50 deg C., at which time the flow of chloroethene was begun at a rate of about 45 sccm. In addition to continuously feeding the chloroethene to the reactor, methane gas (9.8 standard cubic cm/minute) was supplied to the reactor and used as an internal standard.

After about 5.25 hours, a gaseous effluent exiting the reactor was analyzed by gas chromatography, and determined to correspond by mole % to:

|             |       |
|-------------|-------|
| vinyl fluoride | 4.5%  |
| HFC-152a    | 90.7% |
| chloroethene | 4.0%  |
| HCFC-151a   | 0.8%  |

The reaction was carried out for about 16.3 hours and approximately 127 g of chloroethene were supplied to the reactor. When the contents from the reactor were discharged, about 5.14 gm of water insoluble black tar were recovered from the reactor. This amount of water insoluble black tar corresponds to about 4 % tar per chloroethene feed (by weight). A comparison of Comparative Example 1 and Example 1 or 2 and 3 show that the inventive process can achieve a marked reduction in tar formation.

The following is claimed:

1. A low tar process for producing 1,1-difluoroethane comprising:

a) reacting chloroethene with HF or HCl in a liquid phase in the presence of catalyst in a first reaction zone under conditions sufficient to form at least one of 1,1-dichloroethane and 1-chloro-1-fluoroethane;

b) reacting said 1,1-dichloroethane and 1-chloro-1-fluoroethane with HF in a liquid phase in the presence of catalyst in a second reaction zone under conditions sufficient to form a product stream comprising 1,1-difluoroethane; and c) recovering 1,1-difluoroethane from said product stream.

2. The process of claim 1 wherein the temperature of said first reaction zone is from about 0° C. to about 50° C.

3. The process of claim 1 wherein the temperature of said second reaction zone is from about 50° C. to about 150° C.

4. The process of claim 1 wherein said catalyst comprises tin tetrachloride.

5. The process of claim 1 wherein the catalyst is tin tetrachloride and a) said first reaction zone is maintained at a temperature from about 0° C. to about 50° C. and a pressure of about 0 to 50 psig, and b) said second reaction zone is maintained at a temperature from about 50° C. to about 150° C. and a pressure of about 50 to 400 psig, whereby, 1,1-difluoroethane is recovered substantially free of tar.

6. The process of claim 5 wherein tar formed is less than 0.5 weight % of the chloroethene fed.

7. A process for making 1,1-difluoroethane comprising:

providing an agitated liquid mass comprising HF and SnCl$_4$, heating the agitated liquid mass to a temperature of about 50 to 150 C. under reflux conditions at a pressure of about 50 to 400 psig, withdrawing at least a portion of the agitated liquid mass, adding chloroethene to the withdrawn liquid mass, converting at least a portion of the chloroethene within the withdrawn liquid mass to 1,1-difluoroethane, adding the withdrawn liquid mass to the agitated liquid mass; and, recovering 1,1-difluoroethane from the agitated liquid mass.

8. The process of claim 7 wherein the withdrawn liquid mass is added below the surface of the agitated liquid mass.

* * * * *